(12) United States Patent
Weidner et al.

(10) Patent No.: US 7,773,232 B2
(45) Date of Patent: Aug. 10, 2010

(54) APPARATUS AND METHOD FOR DETERMINING TRENCH PARAMETERS

(75) Inventors: Peter Weidner, Rötz (DE); Alexander Kasic, Dresden (DE); Elke Gehring, Weinböhla (DE)

(73) Assignee: Qimonda AG, Munich (DE)

( * ) Notice: Subject to any disclaimer, the term of this patent is extended or adjusted under 35 U.S.C. 154(b) by 432 days.

(21) Appl. No.: 11/755,063

(22) Filed: May 30, 2007

(65) Prior Publication Data

US 2008/0297765 A1    Dec. 4, 2008

(51) Int. Cl.
*G01B 11/02*    (2006.01)
(52) U.S. Cl. .................. 356/512; 356/504; 356/516
(58) Field of Classification Search .......... 356/504, 356/511, 512, 516
See application file for complete search history.

(56) References Cited

U.S. PATENT DOCUMENTS 5,982,489 A * 11/1999 Shiraishi ............... 356/504
6,204,922 B1    3/2001 Chalmers

* cited by examiner

*Primary Examiner*—Tarifur Chowdhury
*Assistant Examiner*—Jonathon D Cook
(74) *Attorney, Agent, or Firm*—Edell, Shapiro & Finnan, LLC

(57) ABSTRACT

An apparatus includes an evaluating unit and a peak detection unit. The peak detection unit is configured to determine at least one peak parameter of a peak in a Fourier transformed reflection spectrum of infrared radiation reflected off a sample that may comprise trench structures. The evaluation unit is configured to determine from the at least one peak parameter and from a correction value containing information about an effective refractive index of the sample, a trench parameter of the trench structures.

31 Claims, 14 Drawing Sheets

PRIOR ART

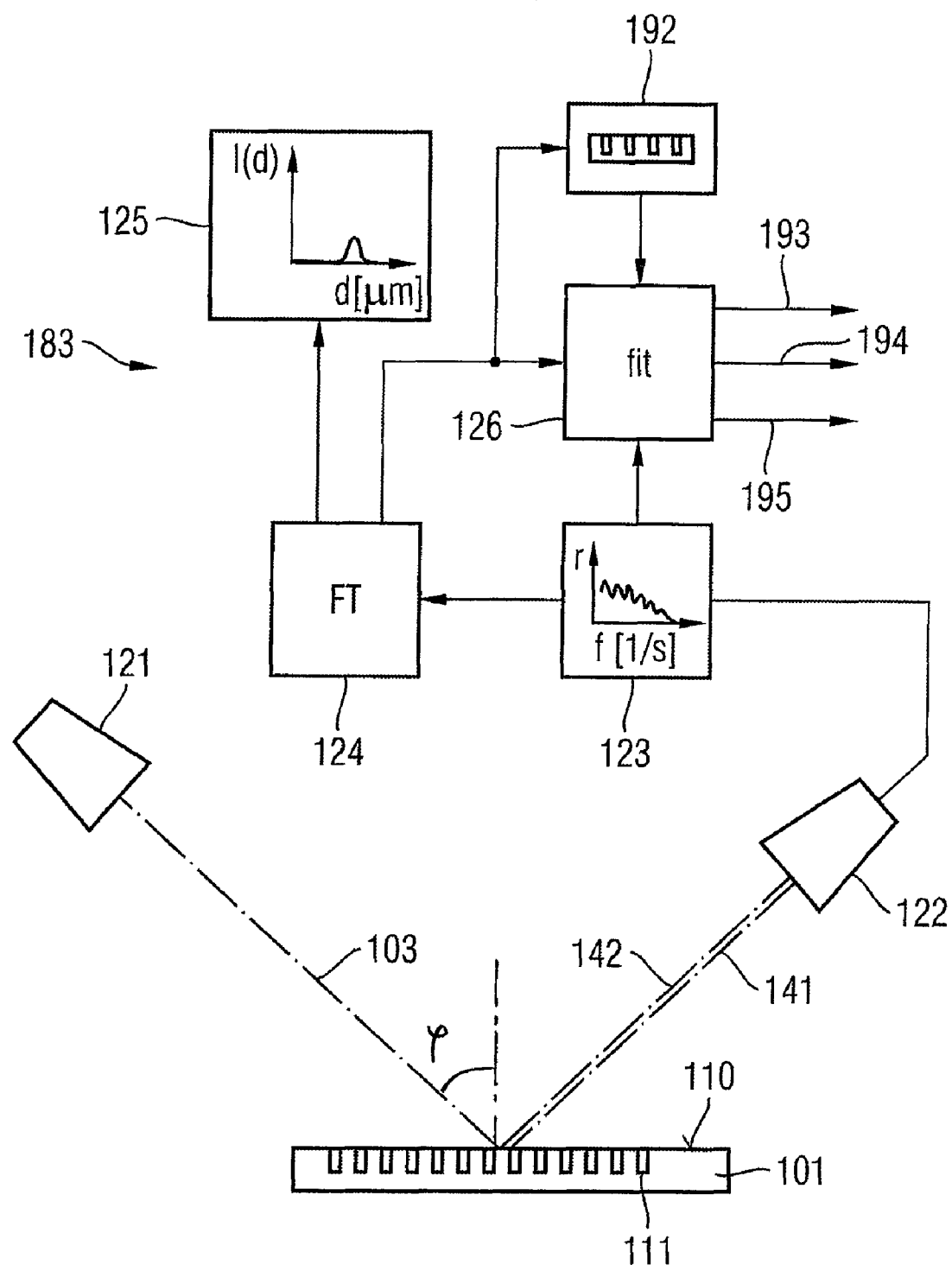

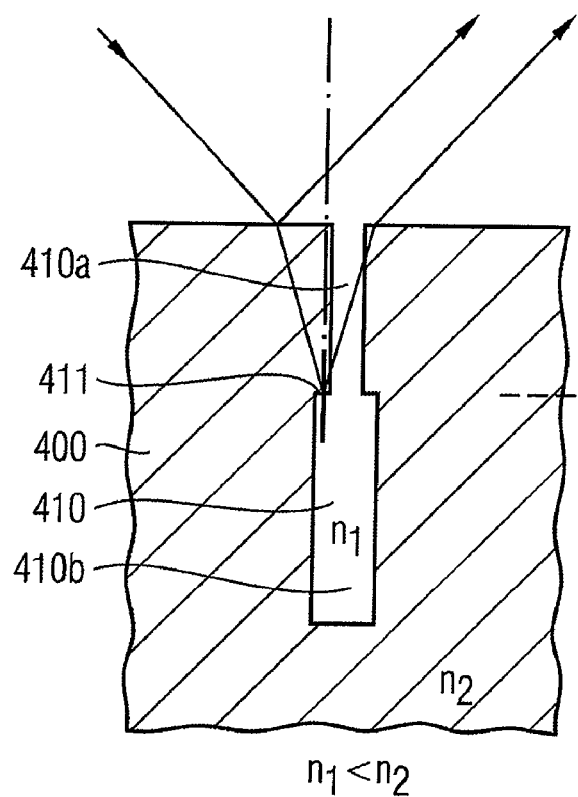
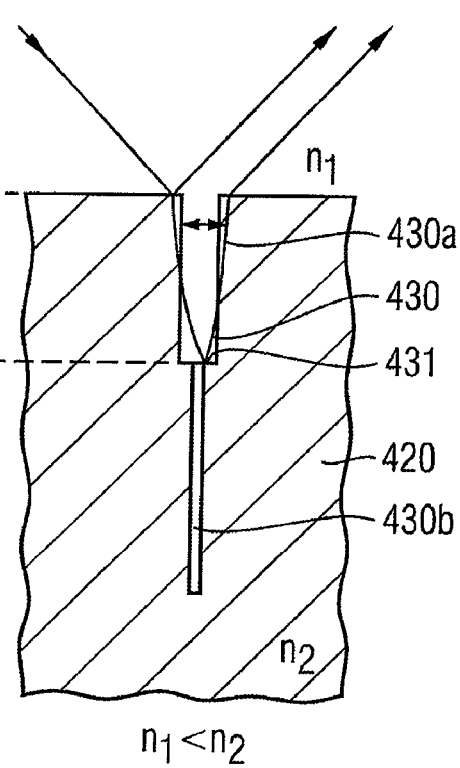
FIG 8A
FIG 8B

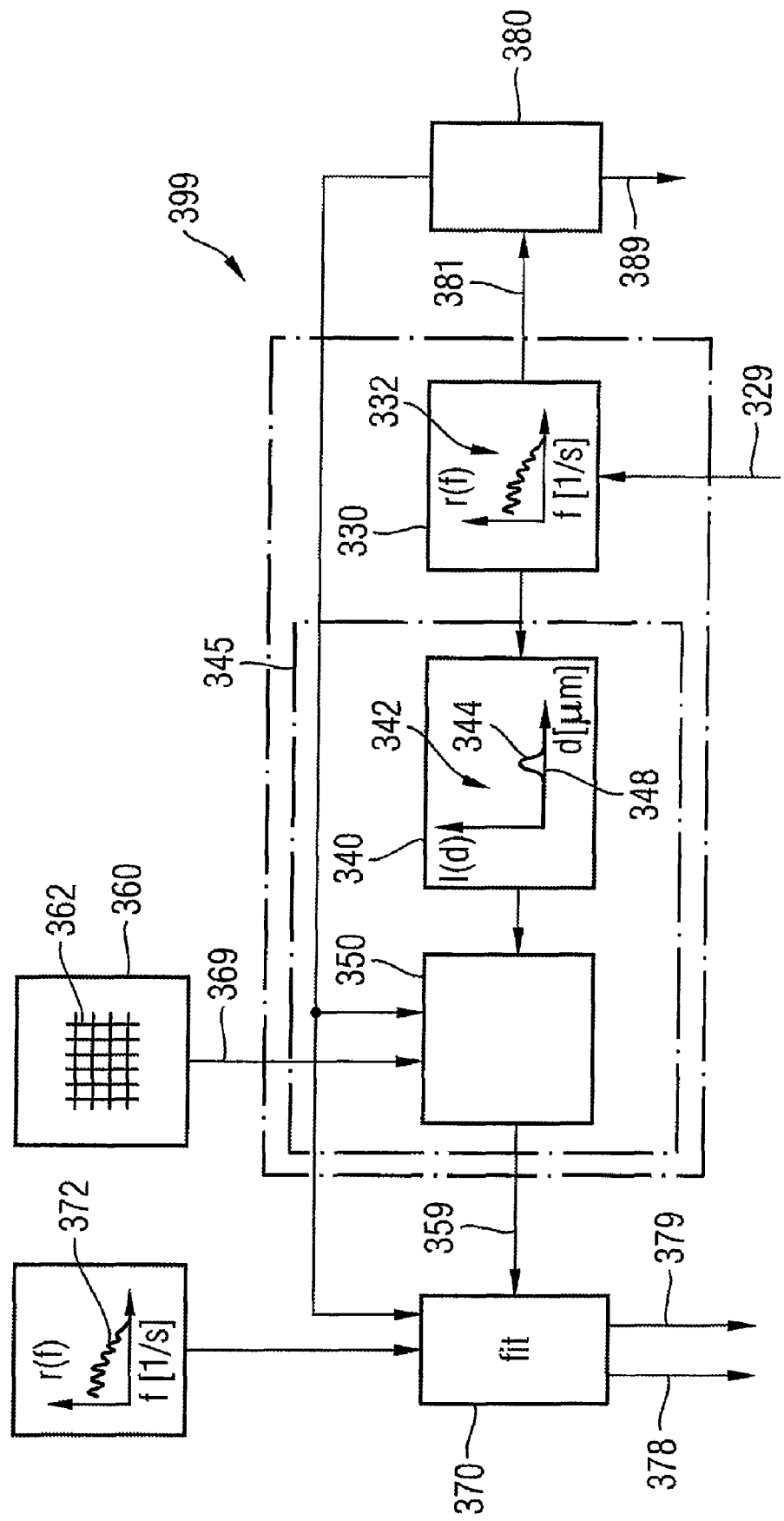

APPARATUS AND METHOD FOR DETERMINING TRENCH PARAMETERS

BACKGROUND

In semiconductor production, spectroreflectometry is used as a non-destructive analyzing method of thin layer systems. An incident infrared radiation beam reflects off a sample, and the intensity of the reflected radiation is analyzed to determine properties of the sample. The incident radiation includes multiple frequency components or is monochromatic with a time-varying frequency. The reflected radiation is analyzed at a plurality of measuring frequencies such that, for example, a reflectance spectrum may be obtained that represents the frequency dependence of the intensity of the reflected radiation.

By analyzing the obtained reflectance spectrum, the thickness of each thin layer in a multiple layer system covering a semiconductor wafer can be determined through model-based algorithms. The model-based algorithms typically use a multiparameter analysis routine to extract the layer parameters. The analysis routine is a fitting method that matches the measured reflectance spectrum with a calculated reflectance spectrum that is obtained by calculating the respective values for a model having equivalent model parameters such as film thickness, refractive index and graded transition-profile thickness. The analysis varies the model parameters until the measured and the calculated reflectance spectrum have the best match.

Further, Fourier-transform infrared (FTIR) reflectance-spectroscopy methods have been developed as metrology tools for characterizing layer systems on a semiconductor wafer. A Fourier-transform infrared apparatus includes a scanning Michelson interferometer, which allows the simultaneous measurement of multiple wavelengths. A beam splitter separates an initial radiation beam into two beams. The first beam has a fixed path length, while the path length of the second beam is periodically varied. The two beams are then recombined such that interference occurs between the beams according to their optical path difference. In this way, an interferogram is obtained that plots the respective radiation intensity against the mirror position, which is related to the optical path difference. Then a Fourier transformation of the interferogram is performed to obtain the reflectance spectrum, which is then analyzed according to various model-based analyzing methods.

For patterned layer systems having a 3D structure, the model-based fitting algorithms become more complicated. The layer parameters and the simulated 3D structure obtained from the model-based fitting algorithm do not always match well with that of the actual layer system. For example, the model-based fitting algorithms often render insufficient results for samples having a 3D structure with high aspect ratio trenches.

SUMMARY OF THE INVENTION

In accordance with the present invention, an apparatus comprises a peak detection unit configured to determine at least one peak parameter of a peak in a Fourier transformed reflection spectrum of infrared radiation reflected off a sample that comprises trench structures, and an evaluation unit configured to determine, from the at least one peak parameter and from a correction value containing information about an effective refractive index of the sample, a trench parameter of the trench structures.

The above and still further objects, features and advantages of the present invention will become apparent upon consideration of the following detailed description of specific embodiments thereof, particularly when taken in conjunction with the accompanying drawings where like numerals designate like components.

BRIEF DESCRIPTION OF THE DRAWINGS

FIG. 6 is a schematic illustration of an apparatus for monitoring trench profiles and for analyzing multi-layer systems covering semiconductor wafers.

FIG. 8A shows a section of a sample comprising a bottle-shaped trench for illustrating a metrology method according to an embodiment.

FIG. 8B shows a section of a sample comprising a trench with a narrowing step for illustrating a metrology method.

FIG. 10 is a schematic illustration of a computing apparatus according to another embodiment of the invention.

DETAILED DESCRIPTION

Figure 1:
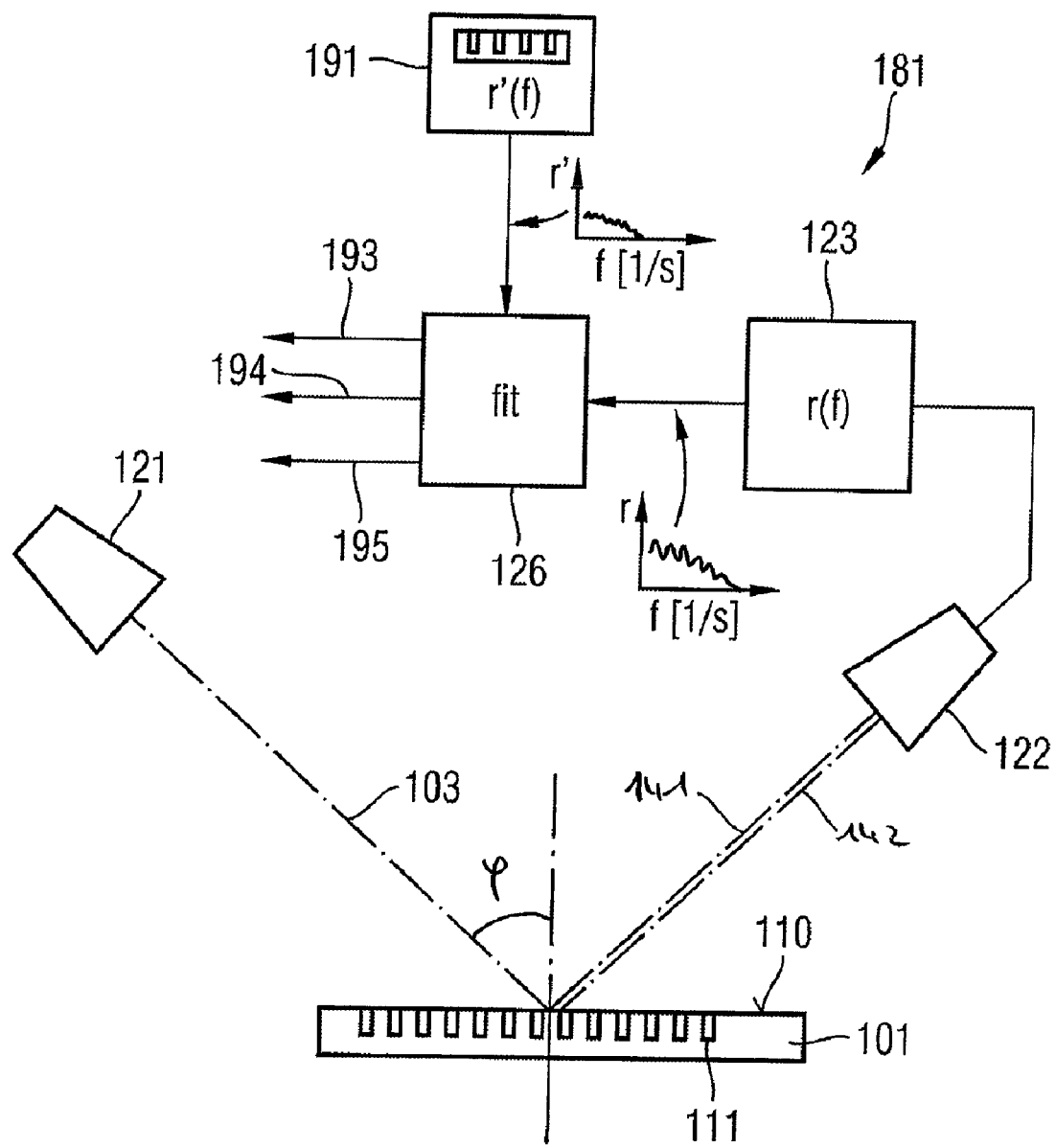
FIG. 1 is a schematic illustration of a conventional apparatus for spectrometrologic analysis of multi-layer systems covering semiconductor wafers.

Referring to FIG. 1, a conventional spectrometrologic analyzing apparatus 181 includes a radiation-emitting unit 121 that emits infrared radiation comprising a plurality of measuring frequencies and irradiates a section of a pattern surface 110 of a sample 101 with an incident radiation beam 103. Trenches 111 are formed within the sample 101 and adjacent to the pattern surface 110. The incident radiation beam 103 is reflected off different reflective planes within the sample 101.

Each reflective plane generates reflected radiation beams 141, 142.

The reflected radiation beams 141, 142 are detected via a radiation detection unit 122 of apparatus 181 and are then analyzed by an analyzer unit 123 of apparatus 181. A reflectance spectrum r(f) is obtained relating a reflectance value to each measuring frequency. The reflectance spectrum r(f) comprises all information of a layer configuration and a 3D structure of at least an upper section of the sample 101, wherein the upper section is oriented to the pattern surface 110.

Further, a reflectance spectrum r'(f) is simulated on the basis of an approximate model of the layer configuration and the 3D structure. A model-based fitting unit 126 approximates the calculated reflectance spectrum r'(f) as close as possible to the measured reflectance spectrum r(f), wherein the layer configuration parameters that form the basis of the calculated model are varied. The model based fitting unit 126 is configured to execute a fitting algorithm. The fitting algorithm evaluates those parameters 193, 194, 195 that correspond to the best matching simulated reflectance spectrum r'(f). These parameters are regarded as describing the actual layer configuration and 3D structure at best and are provided as output by the model-based fitting unit 126.

Figure 2:
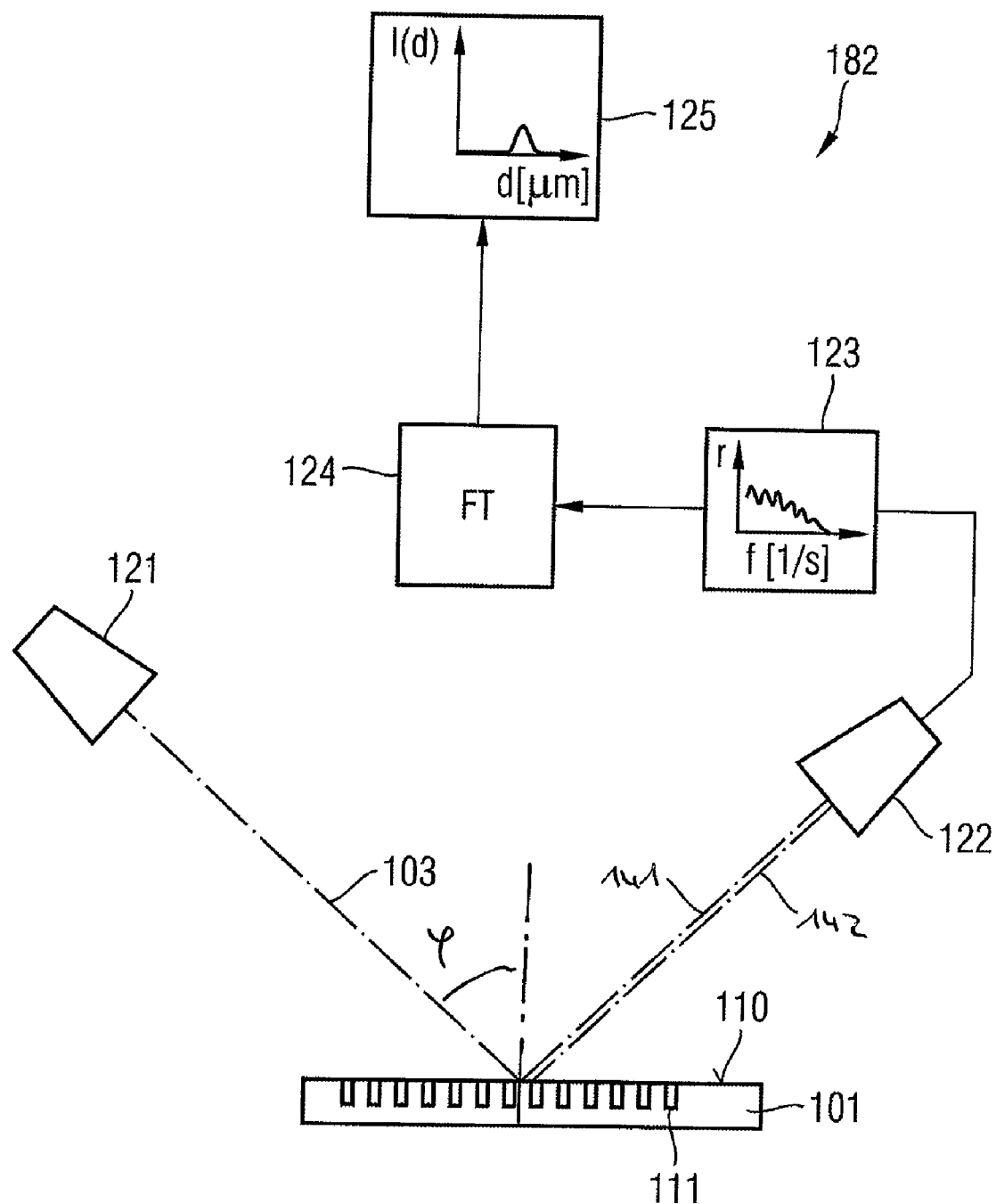
FIG. 2 is a schematic illustration of an apparatus for monitoring trench profiles.

With reference to FIG. 2, a spectrometrologic apparatus 182 for monitoring trench profiles is described. The apparatus 182 may include a radiation-emitting unit 121 for emitting infrared radiation 103 that irradiates a section of a pattern surface 110 of a sample 101 as an incident radiation beam. The emitted infrared radiation 103 comprises a plurality of measuring frequencies and may be a monochromatic radiation, the frequency of which varies with time, or a polychromatic radiation with a continuous spectrum. The measuring wavenumber may range from about 400 cm$^{-1}$ to 7000 cm$^{-1}$. According to an embodiment, the measuring wavenumber may range from about 700 cm$^{-1}$ to 5500 cm$^{-1}$. According to a further embodiment, the emitted infrared radiation may have a known polarization state, and may be, for example, linearly polarized.

The sample 101 may be a semiconductor wafer from which semiconductor memory devices are obtained. The trenches 111 (e.g., used for the formation of trench or trench-in-oxide capacitors) are formed within the sample via an etch process, wherein a top layer may act as a hardmask. The incident radiation beam 103 is reflected off a plurality of reflective planes within the sample 101. Such reflective planes may be: the pattern surface 110, an interface between the top layer and a semiconducting section of the sample 101, the trench bottoms and further interfaces between portions of the trenches 111 with differing structural properties. Each reflective plane corresponds to reflected radiation beams 141, 142 respectively.

The reflected radiation beams 141, 142 are detected by the radiation detection unit 122 and analyzed by the analyzer unit 123 of the apparatus 182. In this way, a reflectance spectrum r(f) may be obtained that relates a reflectance value to each measuring frequency.

When the reflected radiation beams 141, 142 are in phase, they will add constructively. This condition is fulfilled when the effective optical path difference of the beams 141, 142 is an integer multiple of the wavelength. Conversely, when the reflected radiation beams 141, 142 are out of phase they will add destructively. This condition is fulfilled when the effective optical path difference is an integer half (i+½) multiple of the wavelength. The effective optical path difference equals 2*d*n*cos φ, wherein d represents the distance between two reflective planes, φ is the incident angle of the beam 103, and n is the refractive index of the material between the two reflective planes.

The reflected radiation frequency spectrum exhibits periodicities which are representative of the depth of reflective planes in the sample.

The obtained reflectance spectrum r(f) contains inherently characterizing parameters (e.g., refractive indices and layer thicknesses) of a layer configuration and a 3D structure of an upper section of the sample 101.

If the polarization state of the incident radiation beam 103 is known, additionally or alternatively, the polarization state of the reflected radiation beams 141, 142 may be measured and analyzed.

Linearly polarized radiation, when reflected off the sample 101, will change its state to be elliptically polarized. From the shape and orientation of the ellipse and from the polarization state of the incident radiation beam 103, a relative phase change delta(f) and a relative amplitude change psi(f) may be obtained and may be used to calculate, by way of example, the refractive index, thickness and shape of films and/or layers within the sample 101.

A processor 124 of the apparatus 182 performs a Fourier transformation of: the obtained reflectance spectrum r(f), the relative phase change spectrum delta(f) and/or the relative amplitude change spectrum psi(f), wherein a Fourier spectrum is obtained respectively. The Fourier spectrum may be interpreted as a representation of the periodicity of a frequency response or, as the periodicity correlates to an optical distance and to a distance between two reflective planes, as a "thickness spectrum".

The output unit 125 of apparatus 182 outputs the values of the Fourier spectrum. The Fourier spectrum may be provided as a table or as a diagram I(d) with an amplitude I as a function of the inverse of the frequency, which has the dimension of a length. The optical interference is a result of phase differences in light reflected from different layers of the sample. Optical interference is indicated by the oscillations in the reflected spectrum data. To detect the occurrences of the oscillations, a Fourier Transformation is applied on the reflectance spectrum, and the peak parameters of the Fourier Transformation are determined.

In general, the reflected spectrum has a periodic component giving rise to a peak in the Fourier spectrum. Thus, the Fourier spectrum carries information concerning the occurrence and characteristics of reflective planes. A first overview about the characteristics of a sample, such as a semiconductor wafer as described above, may be obtained without modeling. Processes that may be characterized by the occurrence of reflective planes can easily be qualified allowing a quick response to process deviations and fast process control. The occurrence of steps in a trench profile may be easily detected.

Figure 3:
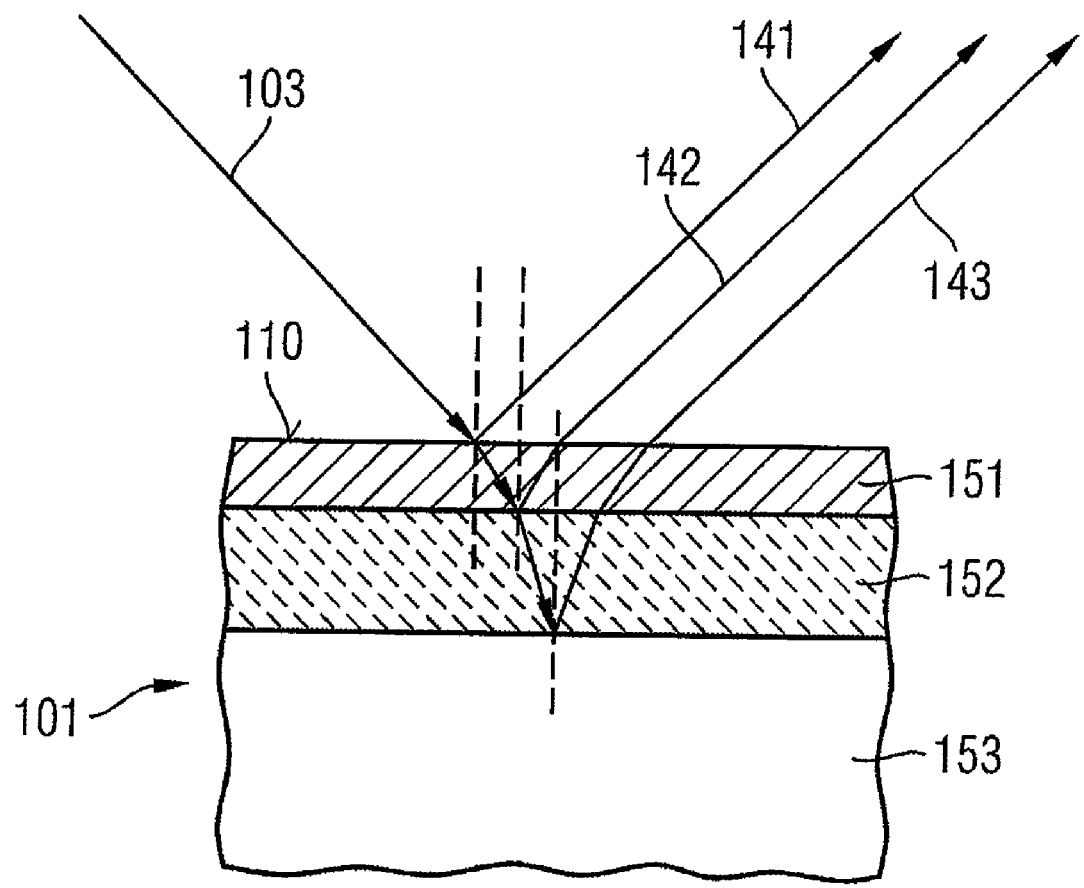
FIG. 3 is a cross-sectional view of a multi-layer system for illustrating schematically the mode of operation of a spectrometrological analyzing apparatus.

FIG. 3 illustrates, in general, the mode of operation of a spectrometrologic analyzing apparatus via a cross-sectional view of a sample 101 including a multi-layer system with a first layer 151 and a second layer 152 on top of a substrate 153. An incident radiation beam 103 is partially reflected off a pattern surface 110 of the sample 101. The non-reflected portion of the incident radiation beam 103 is partially reflected off an interface plane between the first layer 151 and the second layer 152, and a further portion is reflected off an interface plane between the second layer 152 and the substrate 153. As different substances absorb, reflect or emit radiation in different ways, the reflected radiation beams 141, 142, 143 contain information about the materials of the layers 151, 152, 153 like effective refractive index and thickness.

Referring to FIGS. 4A to 4C and FIGS. 5A to 5C, a method for monitoring trench profiles in a semiconductor wafer is described via two schematic cross-sectional views of a substrate 101 having trenches 111 of different profiles.

Figure 4A:
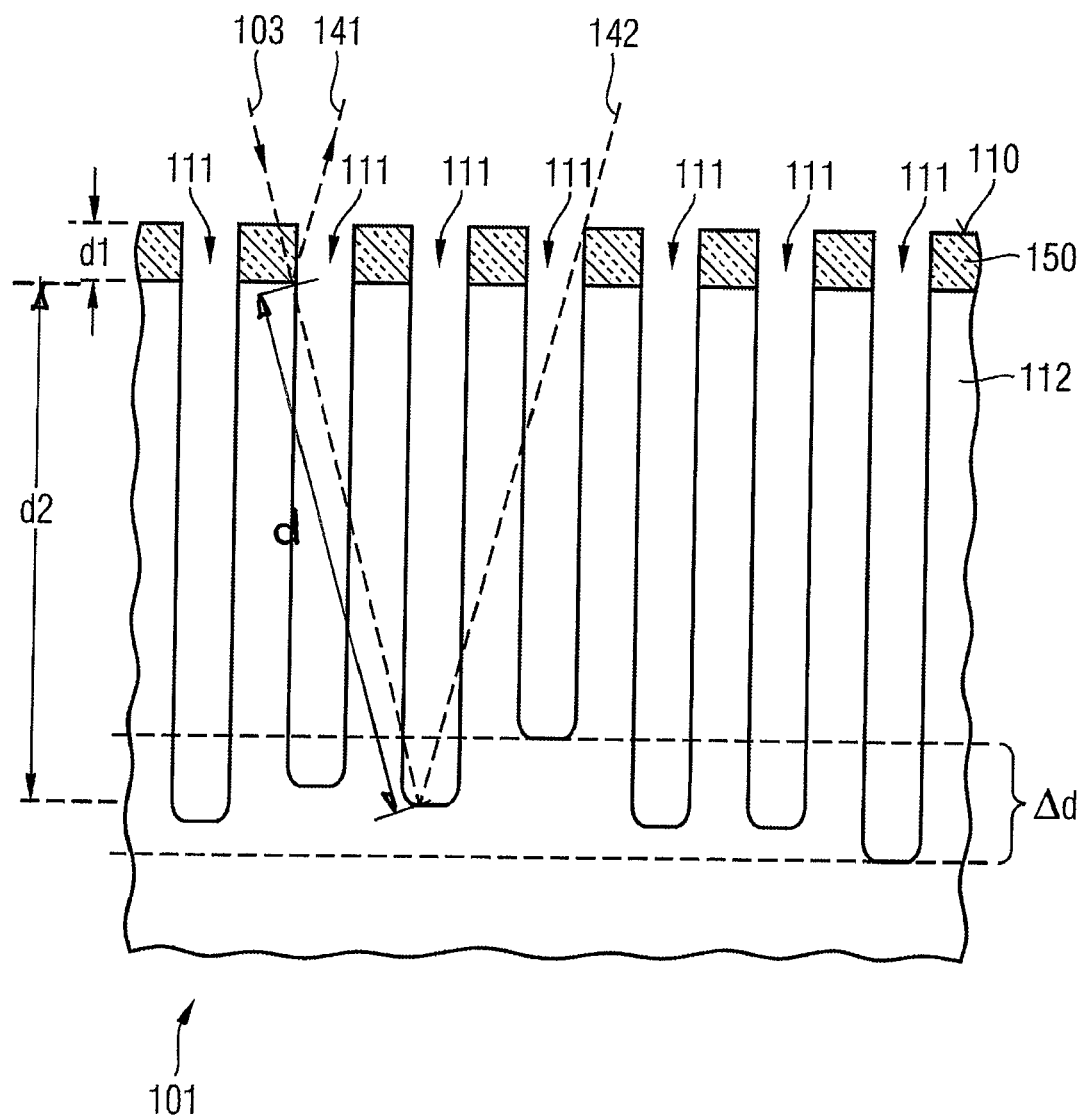
FIG. 4A is a simplified cross-sectional view of a section of a sample comprising trenches with smooth sidewalls for illustrating schematically a method of monitoring trench profiles.

FIG. 4A illustrates a sample 101 having a pattern surface 110 and trenches 111. The trenches 111 extend from the pattern surface 110 into the sample 101 and have smooth sidewalls without any appreciable roughness or steps. The top layer 150 has a thickness d1 and may comprise silicon nitride. The trenches 111 have an average trench depth d2 that may range up to several micrometers and may have a diameter of less than 110 nanometers. The depth of the trenches 111 may fluctuate by Δd. According to an embodiment, the sample 101 is a silicon wafer from which DRAM devices with trench capacitor or trench-in-oxide-capacitor memory cells may be obtained.

An incident radiation beam 103 irradiates a section of the pattern surface 110. A first portion of the incident radiation beam 103 is reflected off the pattern surface 110. A second portion 141 is reflected off the interface between the top layer 150 and the underlying section 112 of the sample 101. A further portion 142 is reflected off the bottom of the trenches 111.

Figure 4B:
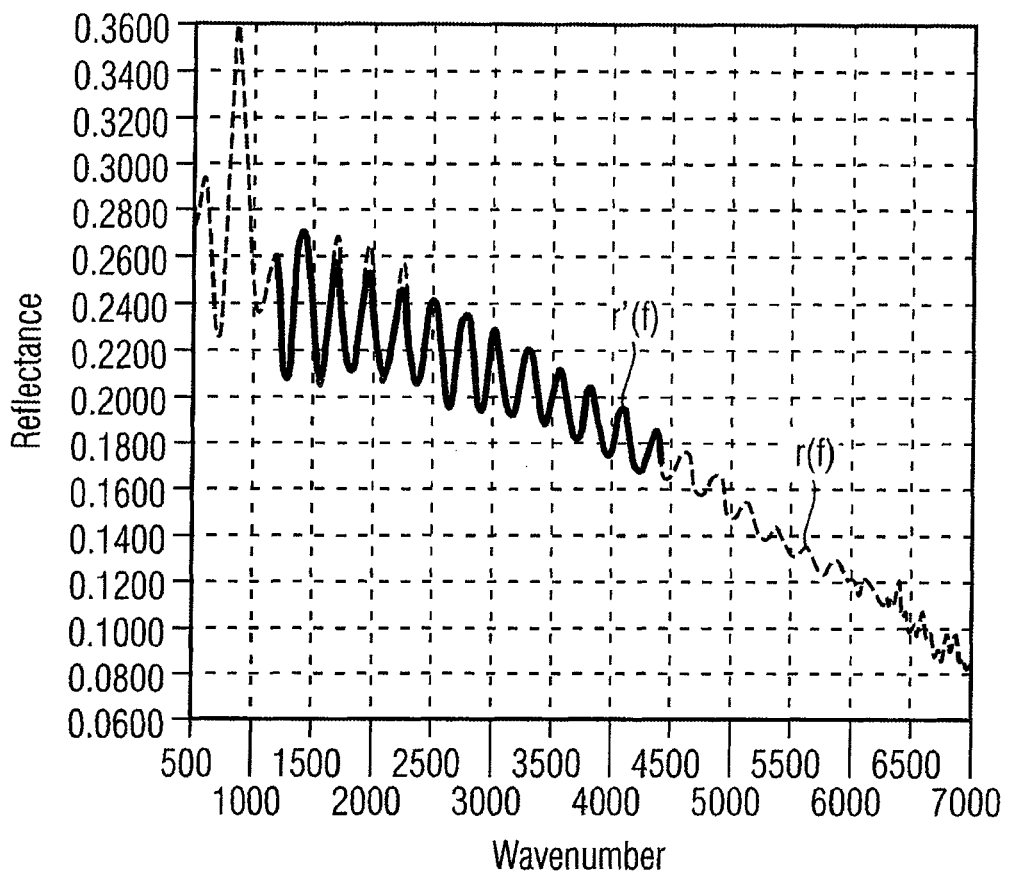
FIG. 4B shows a reflectance spectrum obtained by analyzing the sample shown in FIG. 4A.

FIG. 4B illustrates a diagram with a scaled value of reflectance being plotted against the corresponding measuring frequency. The measuring frequency is scaled in terms of a wavenumber. The dotted line represents a measured reflectance spectrum r(f) being obtained from analyzing the sample of FIG. 4A, e.g., via a detection unit and an analyzer unit of an apparatus according to FIG. 2.

By running a model-based fitting algorithm, a simulated reflectance spectrum r'(f) is obtained. Those parameters that are assigned to that simulated reflectance spectrum r'(f) that matches best with the measured reflectance spectrum r(f) are regarded as best describing the actual sample. The parameters defining the simulated reflectance spectrum r'(f) may closely represent the actual parameters.

Figure 4C:
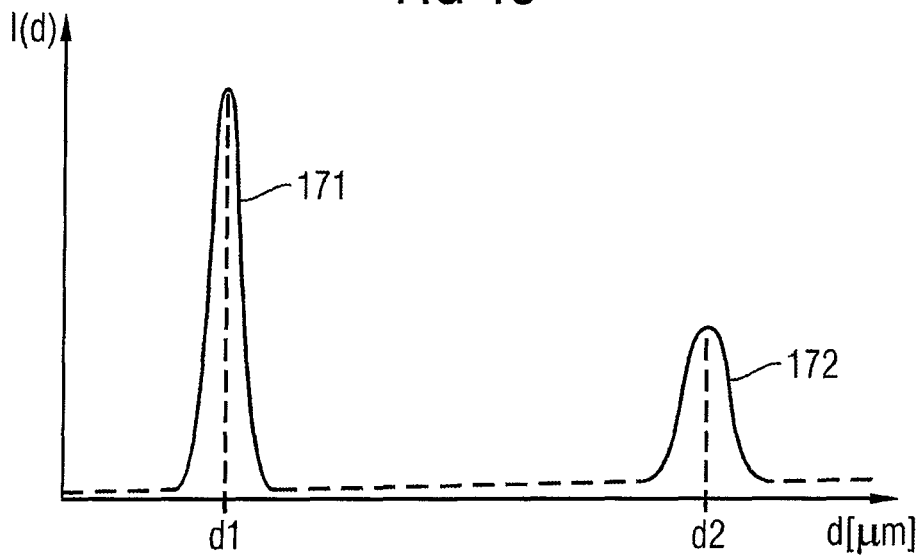
FIG. 4C shows a Fourier spectrum obtained by Fourier transformation of the reflectance spectrum of FIG. 4B.

FIG. 4C shows a Fourier spectrum corresponding to the sample of FIG. 4A. The Fourier spectrum may be considered a thickness spectrum. If the top layer 150 is sufficiently thick, the thickness spectrum exhibits the peak 172 at position d2. The amplitude and width of the respective peak 172 contain information about, for example, the variation of the trench bottom depth d2.

Figure 5A:
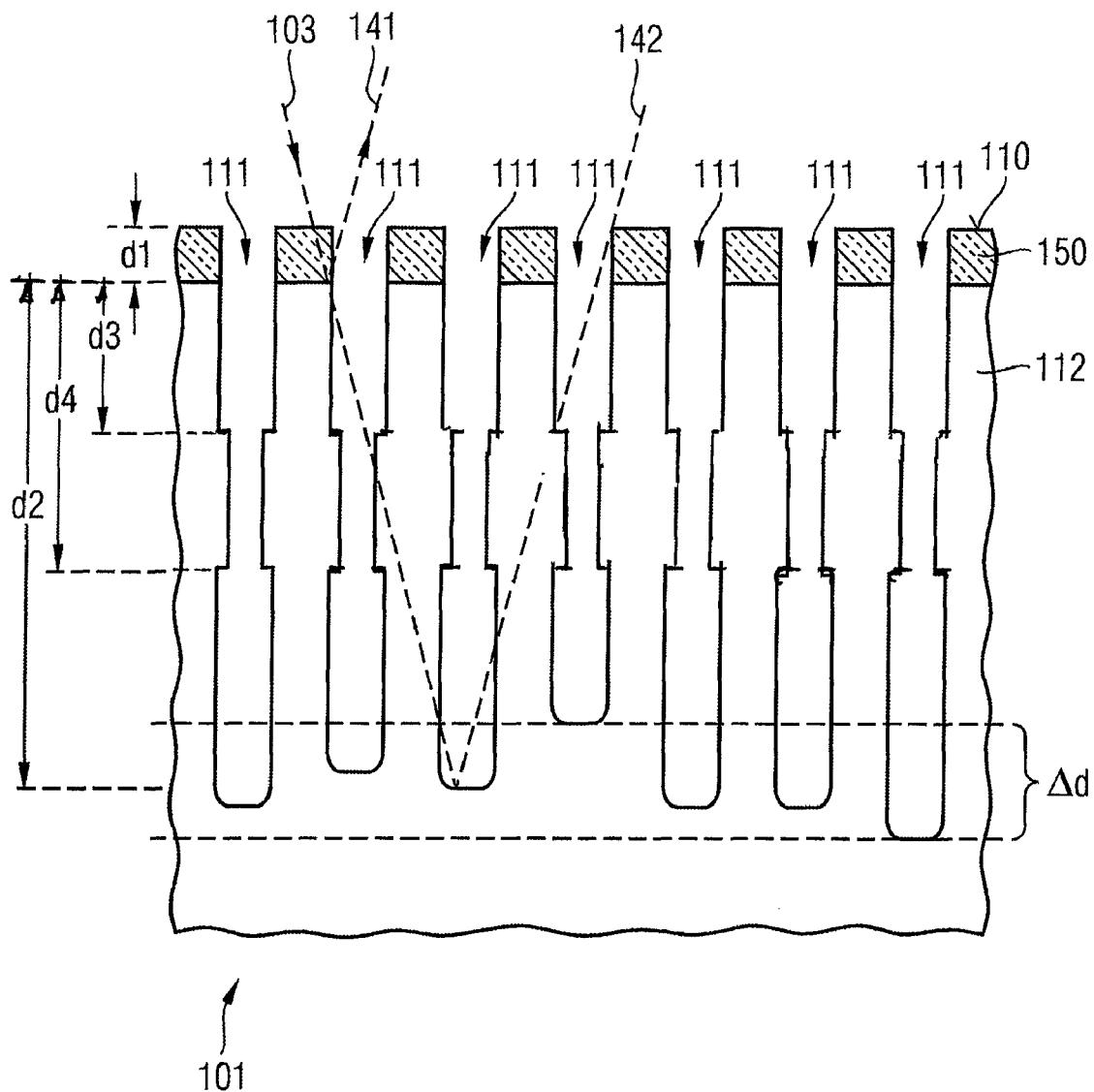
FIG. 5A is a simplified cross-sectional view of a section of a sample comprising trenches with sidewall steps for illustrating schematically a method of monitoring trench profiles.

FIG. 5A illustrates a further sample 101 comprising a pattern surface 110 and trenches 111. The trenches 111 extend from the pattern surface 110 into the sample 101 and have sidewalls with steps at a first average step depth d3 and a second average step depth d4. The incident radiation beam 103 is additionally reflected off the reflection planes represented by the steps at d3 and d4.

Depending upon the process of forming the trenches 111, the trench diameter may increase or decrease at the steps d3 and d4.

Figure 5B:
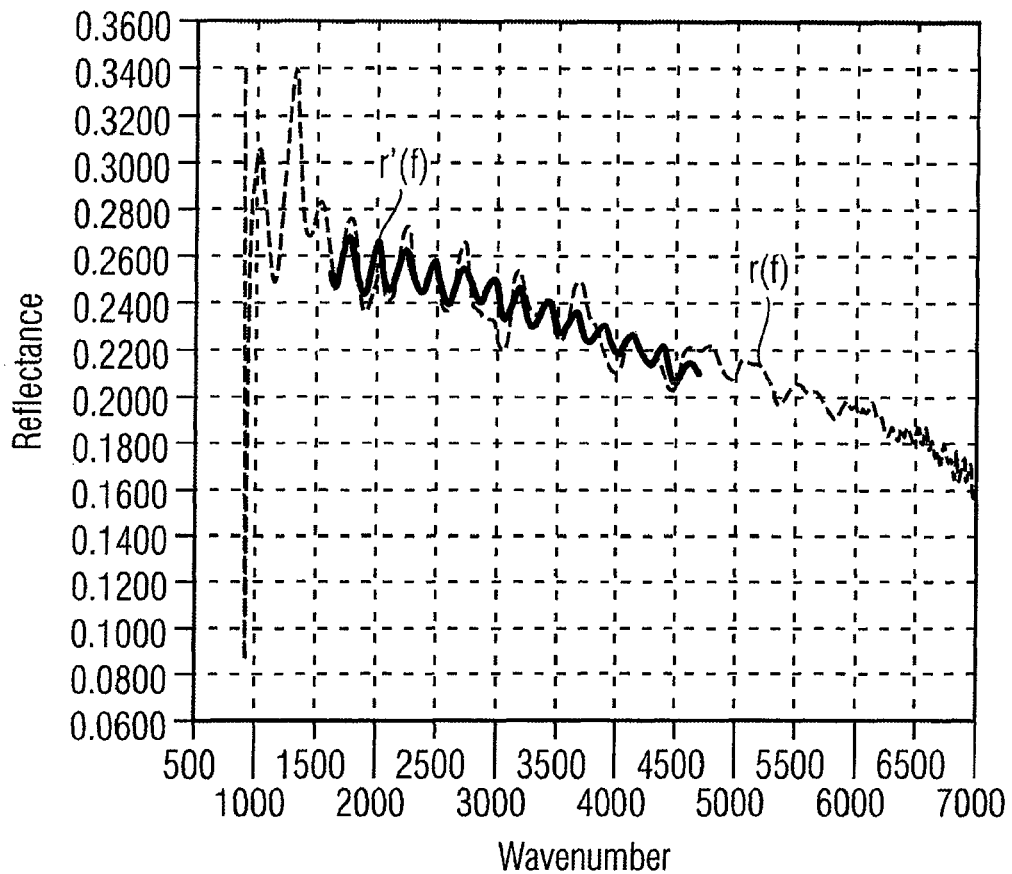
FIG. 5B shows a reflectance spectrum obtained by analyzing the sample shown in FIG. 5A.

FIG. 5B illustrates a diagram with a scaled value of reflectance being plotted against the measuring frequency. The dotted line represents a measured reflectance spectrum r(f) obtained from analyzing the sample of FIG. 5A. The model-based fitting algorithm as described above in relation to FIG. 4B is executed and a further simulated reflectance spectrum r'(f) is obtained.

Due to, inter alia, the steps at d3 and d4, the deviation between the simulated reflectance spectrum r'(f) and the actual reflectance spectrum r(f) may remain large. In this case, the simulated reflectance spectrum r'(f) provides a poor representation of the actual physical features along the sample surface. This indicates that the actual parameters of the sample deviate seriously from the parameters obtained via the model. No exact information about the occurrence and position of the steps can be drawn from the results. No detailed information about the present failure type of the trench formation process may be obtained from the model-based fitting algorithm. Further, time-consuming adaptation of the model-based fitting algorithm or optical post failure analysis methods may be required. A process control loop for correcting insufficient trench sidewall properties may be slow.

Figure 5C:
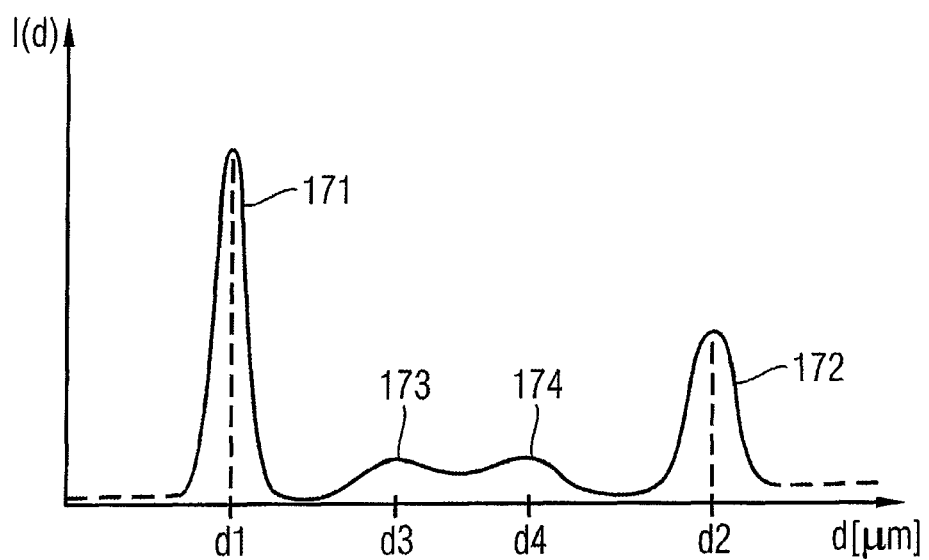
FIG. 5C shows a Fourier spectrum obtained by Fourier transformation of the reflectance spectrum of FIG. 5B.

FIG. 5C shows the Fourier spectrum obtained from analyzing the sample of FIG. 5A. The Fourier spectrum exhibits further peaks 173, 174 at distances d3, d4 corresponding to the depths of the steps. The amplitude and width of each peak 173, 174 may contain information about the trench diameter change at the corresponding step and a step depth variation.

Helpful information concerning the trench formation process can be obtained in the following manner. A quick overview about the characteristics of the trench sidewalls may be obtained without modeling, e.g. by detecting the presence of the peaks 173, 174 in the Fourier spectrum. Processes that may be characterized by predetermined characteristics or occurrence of sidewall steps may easily be examined. A quick response to process abnormalities and fast process control is possible. Steps and roughness of the trench profiles may be qualified in a simple way.

Referring now to FIG. 6, a further exemplary embodiment is described. A spectroreflectometric apparatus 183 comprises the components of apparatus 182 as shown in FIG. 2 and further a model-based fitting unit 126.

A reflectance spectrum r(f) may be obtained in the following manner. The processor 124 of the apparatus 183 performs a Fourier transformation of the obtained reflectance spectrum r(f). The results of the analysis of the Fourier spectrum, e.g. concerning the trench profile, are forwarded directly or via another starting model to a unit 192 which analyzes the Fourier spectrum using a model-based fitting algorithm. Thus, the fitting algorithm is capable of generating a simulated reflectance spectrum r'(f) and allows determining further structural or layer parameters 193, 194, 195.

Figure 7:
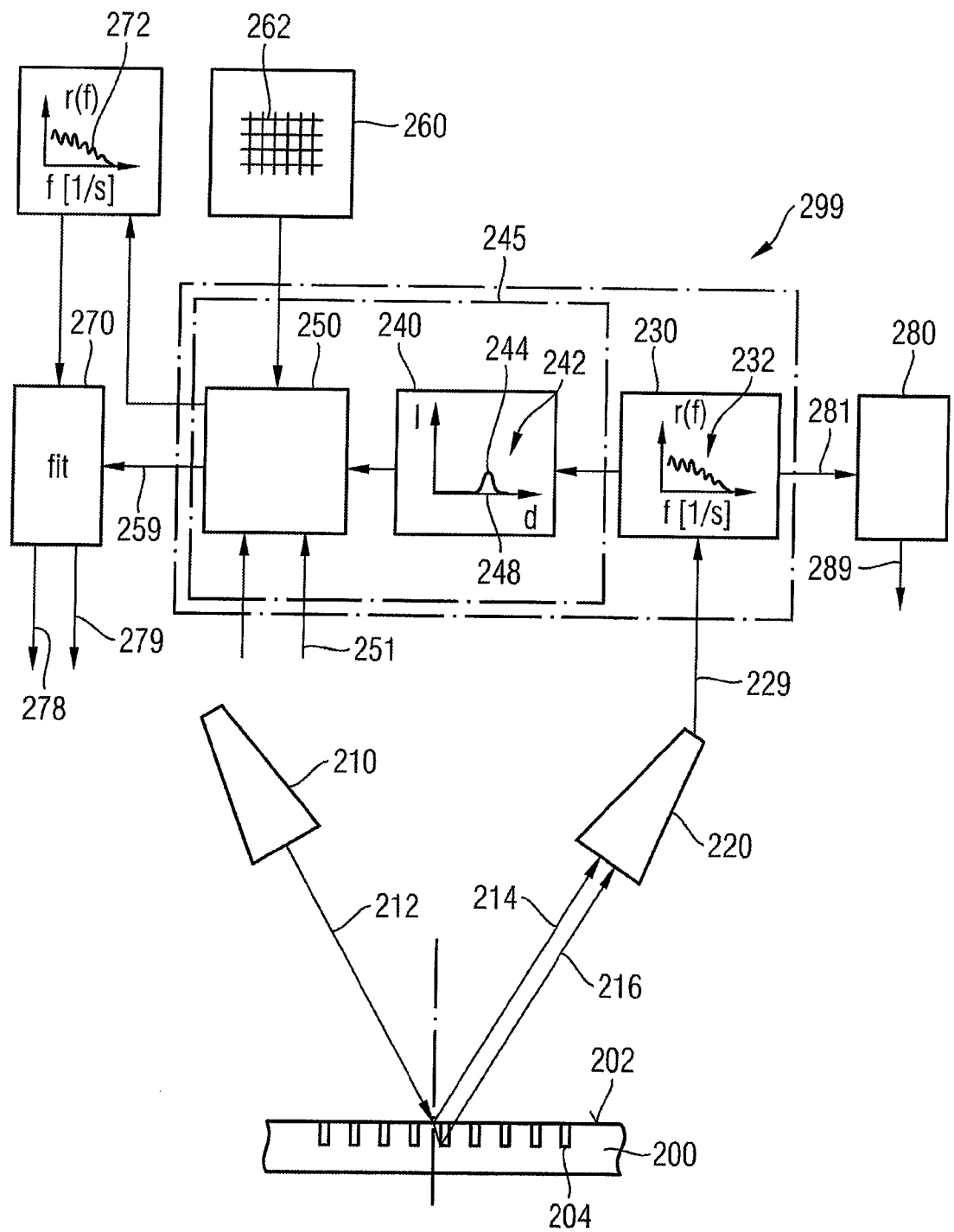
FIG. 7 is a schematic illustration of an exemplary embodiment of a metrology apparatus.

FIG. 7 is a simplified block diagram of an exemplary embodiment of a metrology apparatus 299. The apparatus 299 may comprise an infrared radiation detection device 220, an analyzing device 230, a transformation device 240 and a calculator device 250.

The infrared radiation detection device 220 is configured to detect an infrared radiation 214, 216 that is reflected off a sample 200, wherein the sample 200 may comprise trench structures 204. The infrared radiation detection device 220 may further be configured to output measure values 229 describing parameters of the reflected infrared radiation 214, 216.

The sample may be, for example, a semiconductor substrate such as a single crystalline silicon wafer or a silicon-on-insulator wafer. Besides the trench structures 204, the sample 200 may include other structures that have previously been fabricated, for example doped and undoped sections, epitaxial semiconductor layers supported by a base semiconductor or a base insulator as well as other semiconductor and insulator structures. A cross-section of the trench structures 204 may be a circle, an oval, an ellipse, a square or a rhombus with rounded edges and a cross-sectional area of 400 nm$^2$ or less. According to other embodiments, the trench structures 204 may be line-shaped grooves. The depth of the trench structures 204 may range from nanometers, for example 50 nanometers, to several micrometers, for example 20 micrometers. The trench structures 204 may be air-filled or partially or completely filled with at least one fill material that shows a refractive index differing from that of the surrounding substrate material. The trench structures 204 may be provided to facilitate the formation of sensor arrays, 3D-transistors, micro-mechanical structures or capacitors in silicon or oxide.

Several groups of trench structures 204 may be examined simultaneously, wherein the trench structures 204 of different groups may differ in at least one trench parameter, for example, average trench depth, average trench volume or fill material. The following description refers to a single group of trench structures showing the same target dimensions and comprising the same fill material in order to focus on the principles of the embodiments and to facilitate their understanding.

The analyzing device 230 is configured to determine a reflection spectrum 232 of the reflected infrared radiation 214, 216. The reflection spectrum 232 may be a reflectance spectrum r(f), an amplitude spectrum, a power spectrum, a phase change spectrum, an amplitude change spectrum or a power change spectrum, by way of example. According to the illustrated embodiment, the analyzing device 230 evaluates, from the measure values 229, a reflectance spectrum r(f). The analyzing device 230 may be a processor or part of a processor and may be integral part of a sub-apparatus comprising the infrared radiation detection device 220 and the analyzing device 230 and/or of a sub-apparatus comprising the transformation device 240, the analyzing device 230 and the calculator device 250. According to other embodiments, the analyzing device 230 may be a program or part of a program executed in a processor.

The transformation device 240 is configured to Fourier transform the reflection spectrum 232 for determining a Fourier transformed reflection spectrum 242 of the reflection spectrum 232, for example of the reflectance spectrum r(f).

According to the illustrated embodiment, the transformation device 240 calculates a Fourier transformed reflectance spectrum I(1/f) from the measure values 229. As described above, the peak locations of the Fourier transformed reflectance spectrum are correlated to optical path differences d, such that the Fourier transformed reflectance spectrum may be scaled in terms of a measure of length. Therefore, a peak 244 in the Fourier transformed reflectance spectrum I(d) may correspond to the bottom edge of the trench structures 204. An optical path difference occurs between a first portion of the reflected infrared radiation 214, which is reflected off the upper edge 202 of the sample 200, and a second portion of the reflected infrared radiation 216, which is reflected off the bottom of the trench structures 204.

The transformation device 240 may be a processor or part of a processor and may be integral part of a sub-apparatus comprising the transformation device 240, the analyzing device 230 and the calculator device 250. According to other embodiments, the transformation device 240 may be a program or part of a program executed in a processor.

The calculator device 250 may be a computing apparatus that comprises an evaluating unit and a peak detection unit. The peak detection unit is configured to determine at least one peak parameter of a peak in Fourier transformed reflection spectrum of infrared radiation reflected off a sample that may comprise trench structures. The evaluation unit is configured to determine from the at least one peak parameter and from a correction value containing information about an effective refractive index of the sample, a trench parameter of the trench structures.

Thus, the calculator device 250 is configured to calculate a trench parameter of the trench structures, for example average trench depth, trench depth variation, average trench volume, trench volume variation, average upper edge depth of bottle-shaped trenches and the variation thereof, from parameters of a corresponding peak in the Fourier transformed reflection spectrum and from the effective refractive index of a section of the sample above a bottom edge of the trench structures.

For example, the calculator device 250, or its evaluator unit may be configured to calculate an average trench depth based upon an optical path difference between portions of the reflected infrared radiation 214, 216, wherein the optical path difference is proportional to the distance between the respective reflective planes and the effective refractive index of the section of the sample between them.

For example, the calculator device 250, or its evaluator unit may be configured to calculate the optical path difference from determining the position of the peak in the Fourier transformed reflection spectrum that is assigned to the reflection plane represented by the bottom edge of the trench structures.

The position of the peak 244 is a measure of the distance between the bottom edge of the trench structures 204 and the upper edge 202 of the sample 200, wherein the position depends also on the effective refractive index of the section of the sample between the bottom edge of the trench structures 204 and the upper edge 202 of the sample 200. In other words, the peak position depends on the ratio of the total trench volume to the volume of the material embedding the trench structures 204. The calculator device 250 may be, for example, configured to calculate the average trench depth on basis of the optical path difference and the effective refractive index or an equivalent value, for example the correction value.

According to a further embodiment, the metrology apparatus 299 may further comprise a storage unit 260 that holds a correlation information 262 between trench geometry parameters and at least one peak parameter, such as amplitude, width or position, in Fourier transformed reflection spectra of a plurality of samples. By way of example, the correlation information 262 may be obtained through a calibration method that comprises collecting the Fourier transformed reflection spectra of the plurality of samples and recording the actual average trench depths and/or average trench volumes through conventional methods, for example post failure methods such as scanning electron microscopy (SEM) or top-down CD-SEM. If the trench structures are further processed to form capacitors, a capacitance measurement may be correlated to the volume measurement, as the capacitance of a capacitor is proportional to the effective electrode area, which in turn may be estimated from the measured trench volume.

The correlation information contains at least inherent information about the effective refractive index of the respective sample, for example the correction value as described above, and may be held as a kind of table or a formula/set of formulas or as a data set adapted to be fed forward into a fitting algorithm, by way of example. A suitable formula for the average depth of a trench filled by a certain material (e.g. air, resist) is, by way of example, $d=pp/[2*(n2+n1*f)]$, wherein pp corresponds to the position of a peak corresponding to the bottom trench edge, f is the average fraction of the fill material (e.g. $f=(tv+bv)/2$ for air-filled trenches, with tv=top void, bv=bottom void), n2 is the refractive index of the material embedding the trench structures, for example silicon, $n1=n(fill)-n2$ (with n(fill) being the refractive index of the fill materials, for example air). For air-filled trenches in a Si host, n2=3.4 and n1=−2.4. For the sake of simplicity, a linear mixing of the refractive indices is employed here. Bv is a measure of the cross-sectional area of the trench structures at the bottom edge and tv is a measure of the cross-sectional area the trench structures at the top edge. Tv may be derived from other measurements and bv may be derived from the amplitude of the corresponding peak. The calculator device 250 may further be configured to calculate the average trench depth by linking the correlation information 262 with the optical path difference obtained from the Fourier transformed reflection spectrum.

According to a further exemplary embodiment, the calculator device or its evaluator unit may be configured to determine an average trench volume via a peak shift resulting from filling the trench structures with an auxiliary fill. In the following example, the position of a peak corresponding to the bottom edge of air-filled trench structures in a silicon host with a refractive index of 3.43 is determined and stored. The refractive index of air is 1.00 and the ratio of the trench volume to the total volume may be, for example, 20 percent which results in an effective refractive index of the section of the sample above the bottom edge of 3.10 employing effective medium theory (averaging dielectric functions $\in = n^2$). Filling the trench structures with a fill material with a refractive index of 1.50 increases the effective refractive index to 3.14 and shifts the respective peak in the Fourier transformed reflectance spectrum. The shift may be calibrated via one of the methods described above. Likewise, the average trench depth and volume can be obtained from a combination of measurements of trench structures with the same depth, but different fill materials, if the refraction indices of the host and fill materials are known.

According to other embodiments, the infrared radiation detection device 220 may be configured to measure the intensity and/or polarization state of infrared radiation 214, 216 reflected off the sample 200.

The metrology apparatus may further comprise an infrared radiation emitting device 210 configured to irradiate the sample 200 with infrared light 212. According to other embodiments, the infrared radiation may be linearly polarized or unpolarized.

As the correlation information contains information about the ratio of trench volume to host volume, the calculator device 250 may also be configured to calculate and output the average trench volume on basis of the correlation information and the specific refractive indices of the materials of the host and the trench fill, wherein the information concerning the materials and the refractive indices may be supplied to the calculator device 250 via further input units 251.

The metrology apparatus 299 may further comprise a model-based fitting device 270 configured to receive results 259 from the calculator device 250 and to match parameters of a model of sample 200 on base of the results 259 output by the calculator device 250. The results 259 of the analysis of the Fourier spectrum concerning, for example, average trench volume, average trench depth, sidewall steps and roughness may be forwarded directly into a model-based fitting algorithm or via another starting model 272. Thus, the fitting algorithm is capable of generating a more accurate simulated reflectance spectrum r'(f) and may allow determining further topographic or layer parameters 278, 279 of the sample 200 more precisely.

According to another embodiment, the metrology apparatus 299 may comprise further a step analyzing device 280 configured to determine an inward/outward orientation of steps within the trench structures 240 via the phase of a reflectance spectrum r(f) based upon a method as described below in relation to FIGS. 8A to 8C.

FIG. 8A shows a section of a sample with a trench structure 410 embedded in a mold 400. According to the illustrated example, the trench structure 410 is bottle-shaped with a narrow upper portion 410a, a wide lower portion 410b and an outwardly oriented step 411 at the junction between them. A material forming the mold 400 shows a refractive index that is higher than that of a material filling the trench structure 410. The host material is, for example, silicon with a refractive index of about 3.4. The trench structure 410 is, for example, filled with air or a gas with a refractive index of less than 1.1. At the interface from the high reflective index material to the low reflective index material, no phase change occurs in the reflected infrared radiation.

FIG. 8B shows a further sample with another trench structure 430 embedded in a mold 420. The trench structure 430 shows a wide upper portion 430a, a narrow lower portion 430b and an inwardly oriented step 431 at the junction between them. Again, a material forming the mold 420 has a high refractive index, for example 4, and that material filling the trench structure 430 has a low refractive index of, for example less than 1.1. At the interface from the low reflective index material to the high reflective index material, a phase change of 180 degree occurs in the reflected infrared radiation.

The phase change in case of FIG. 8B results in a reflectance spectrum that is, with respect to a mean line, inverted to that of the sample of FIG. 8A.

According to another embodiment, the calculator device 250 or its evaluator unit may be further configured to calculate a volume expansion of trench structures on the basis of a shift of a peak in the Fourier transformed reflection spectrum.

Figure 9C:
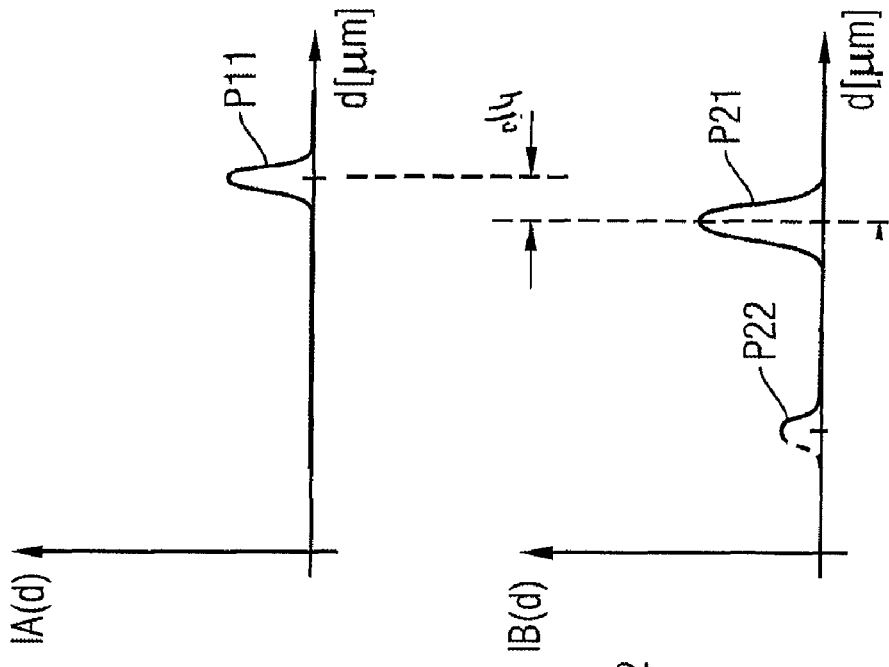
FIG. 9C shows the Fourier spectra obtained by Fourier transformation of the reflectance spectra obtained by analyzing the samples shown in FIGS. 9A and 9B.
Figure 9A:
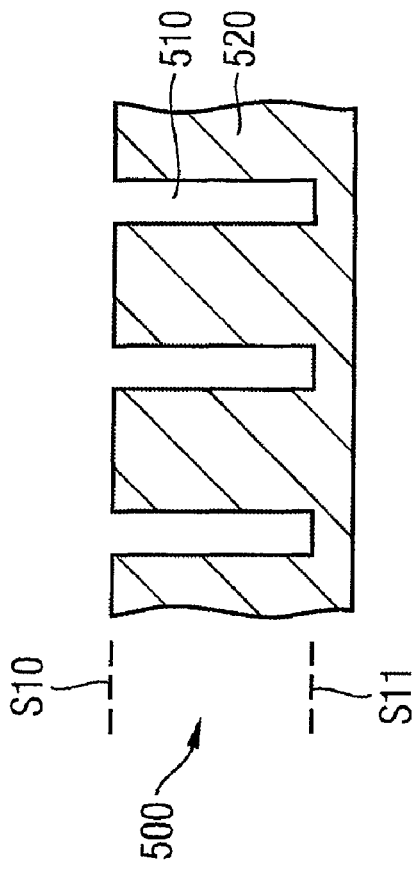
FIG. 9A is a schematic illustration of a sample comprising trenches.
Figure 9B:
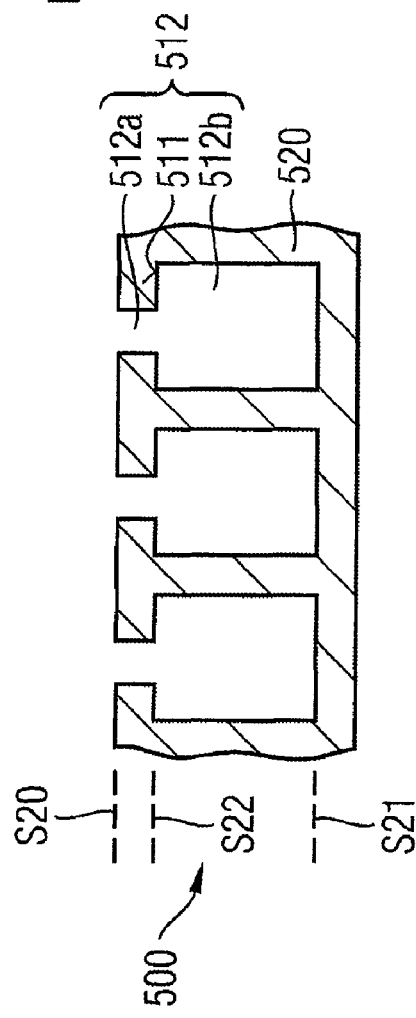
FIG. 9B is a schematic illustration of the sample of FIG. 9A after a bottle-shaped volume expansion of the trenches.

FIGS. 9A to 9C illustrate a method of determining a volume expansion coefficient. FIG. 9A shows a sample 500 with trench structures 510 confining to an upper surface of the sample 500 and with a mold 520 embedding the trench structures 510. A top surface of the sample 500 is effective as a first reflective plane S10 and the bottoms of the trench structures 510 may be considered as fragmented reflection plane S11. The trench structures 510 may be expanded, for example via a wet bottle etch, in a lower section.

FIG. 9B shows a cross-sectional view of the sample 500 comprising expanded trench structures 512. Each expanded trench structure 512 comprises a narrow upper portion 512a and a wide lower portion 512b. The top surface of the sample 500 after the volume expansion is effective as a reflective plane S20. Steps 511 at the interface between the upper and the lower portion 512a, 512b and the bottom edges of the expanded trench structures 512 are effective as further fragmented reflection planes S22, S21.

The wet bottle etch may be a masked wet etch, wherein the upper portions of the trench structures 510 are covered by an etch mask. Further, the etch may recess the sidewalls of the trench structures 510 more than the bottom edges such that the depth of the trench structures before and after volume expansion may be considered as being essentially equal.

FIG. 9C shows the respective Fourier transformed reflectance spectra. The upper spectrum IA(d) is that of the sample 500 of FIG. 9A and comprises a peak P11 that corresponds to the optical path distance between the reflective planes S10, S11. The position of peak P11 depends on the trench depth and the refractive index which is effective between the reflective planes S10, S11.

The second diagram illustrates the Fourier transformed reflectance spectrum IB(d) of the sample 500 as shown in FIG. 9B. A first peak P21 corresponds to the reflective plane S21 and a second peak P22 corresponds to the reflective plane S22. Though the depth of the trench structures 510, 512 after and before the volume expansion is essentially equal, the peak position P21 differs from that of peak P11. The peak shift d2 results from an alteration of the effective refractive index of the sample between the two reflective planes S21, S22 wherein the alteration is a consequence of the volume expansion. The peak shift d4 is a measure for the volume expansion. The correlation between the peak shift d4 and a volume expansion coefficient may be calibrated via examination of calibration samples as sketched above, by way of example.

FIG. 10 is a simplified illustration of a computing apparatus 399 that comprises a calculator unit 350 which is configured to determine a trench parameter of trench structures in a sample on the basis of peak parameters of peaks in a Fourier transformed reflection spectrum and from a correction value containing information about an effective refractive index of the sample. The computing apparatus may comprise an evaluating unit and a peak detection unit. The peak detection unit is configured to determine at least one peak parameter of a peak in Fourier transformed reflection spectrum of infrared radiation reflected off a sample that may comprise trench structures. The evaluation unit is configured to determine from the at least one peak parameter and from a correction value containing information about an effective refractive index of the sample, a trench parameter of the trench structures.

The computing apparatus 399 may further comprise an analyzer unit 330 which is configured to determine a reflection spectrum 332 of the reflected infrared radiation 329. The reflection spectrum 332 may be a reflectance spectrum, an amplitude spectrum, a power spectrum, a phase change spectrum, an amplitude change spectrum or a power change spectrum, by way of example.

The computing apparatus 399 may further comprise a transformation unit 340 which is configured to determine a Fourier transformed reflection spectrum from the reflection spectrum determined via the analyzer unit 330. The calculator unit 350 may further be configured to determine, from a position of a peak 344 in the Fourier transformed reflection spectrum 342, an optical path difference between portions of the reflected infrared radiation, wherein the peak 344 is assigned to a fragmented reflective plane that corresponds to a bottom etch of the trench structures. The computing apparatus 399 may further comprise a storage unit 360 that holds a correlation information 362. The correlation information links effective refractive indices of a plurality of samples comprising trench structures, or equivalent values containing information about the effective refractive indices and parameters of peaks in Fourier transformed reflection spectra assigned to the pluralities of samples. The calculator device 350 may further be configured to determine at least inherently an effective refractive index of the sample, or an equivalent physical parameter containing the information about the effective refractive index, based upon the correlation information 362.

According to another embodiment, the calculator unit 350 may be configured to evaluate the correction value or the effective refractive index using a model based fitting algorithm. The trench parameter may be an average trench depth, wherein the calculator unit 350 is configured to calculate the average trench depth from the optical path difference and the effective refractive index of the sample between an upper surface and the bottom of the trenches or an equivalent physical parameter containing the information about the effective refractive index. The trench parameter may be, according to another embodiment, an average trench volume, wherein the calculator unit is configured to calculate the average trench volume from the effective refractive index and from the refractive indices of the materials forming the sample between the upper surface of the sample and the bottom of the trench structures. The computing apparatus 399 may further comprise a step analyzer unit 380 that is configured to determine an orientation of steps in the trench structures via the phase of the reflectance spectrum (e.g., where different steps in the trenches are oriented to define trench sidewall sections that extend toward or away from an axial center of the trenches in relation to other peripheral trench sidewall sections). Parameters 381 outputted by the analyzer unit 350 may be supplied to the step analyzer unit 380 which may deliver step information parameters 389.

The computing apparatus 399 may further comprise a model based fitting unit 370 that is configured to calculate parameters of a model on the basis of results 359 outputted by the calculator device 350. The results 359 of the analysis of the Fourier spectrum, for example regarding average trench depth, trench depth variation, average trench volume, trench volume variation, average upper edge depth of bottle-shaped trenches and the variation thereof, profile characteristics, and others may be directly forwarded into a model-based fitting algorithm or may be used in another, improved starting model 372. The fitting algorithm is therefore capable of generating a more precise reflectance spectrum r(f) and may allow determining further topographic or layer parameters 378, 379 of the respective sample more precisely. The computing device 399 or parts thereof may be a processor or part of a processor or a suitable application specific integrated circuit.

Figure 11A:
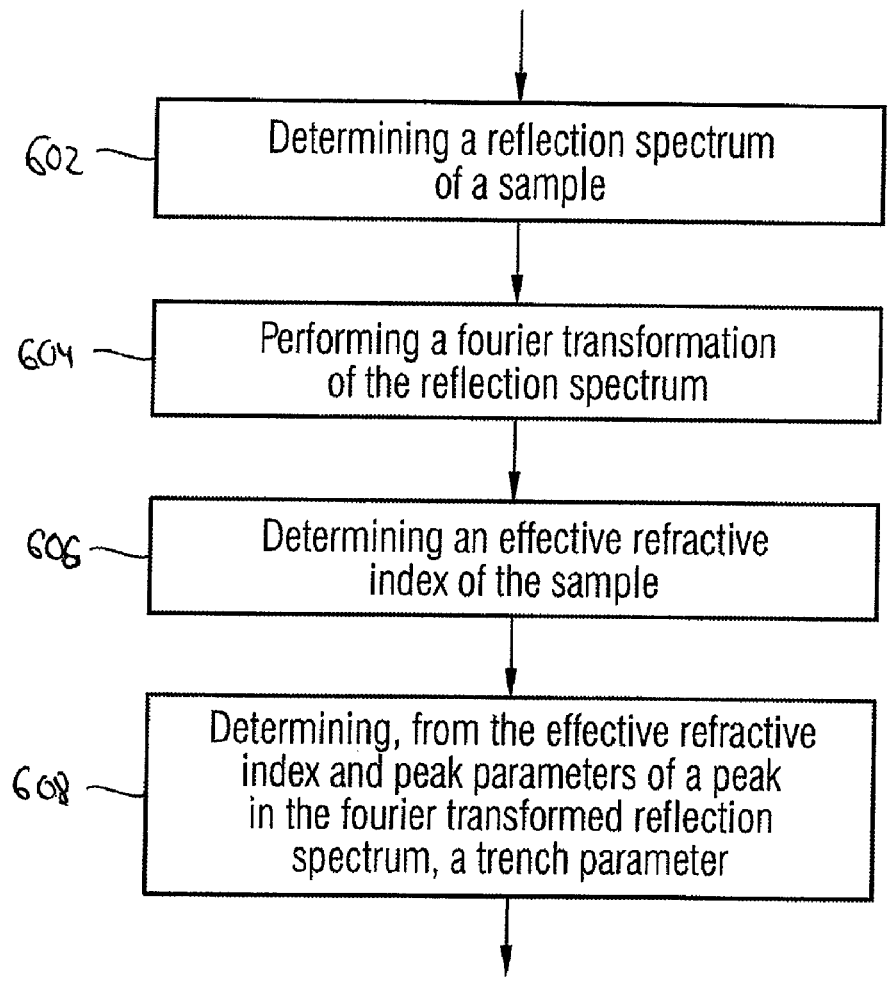
FIG. 11A is a simplified flow-chart of an exemplary embodiment of a metrology method.

FIG. 11A is a simplified flow-chart illustrating a metrology method according to another embodiment of the invention. From a sample comprising trench structures, a reflection spectrum of infrared radiation reflected off the sample is determined (602). The reflection spectrum may be a reflectance spectrum, an amplitude spectrum, a power spectrum, a phase change spectrum, an amplitude change spectrum or a power change spectrum, by way of example. A Fourier transformation of the reflection spectrum is performed to determine a Fourier transformed reflection spectrum (604). Further, at least inherently, an effective refractive index of the sample is determined (606). At least one peak parameter of a peak in the Fourier transformed reflection spectrum is evaluated in order to determine a trench parameter of the trench structures (608), wherein the peak is assigned to a reflective plane that corresponds to an average depth of the bottom edge of the trench structures.

Figure 11B:
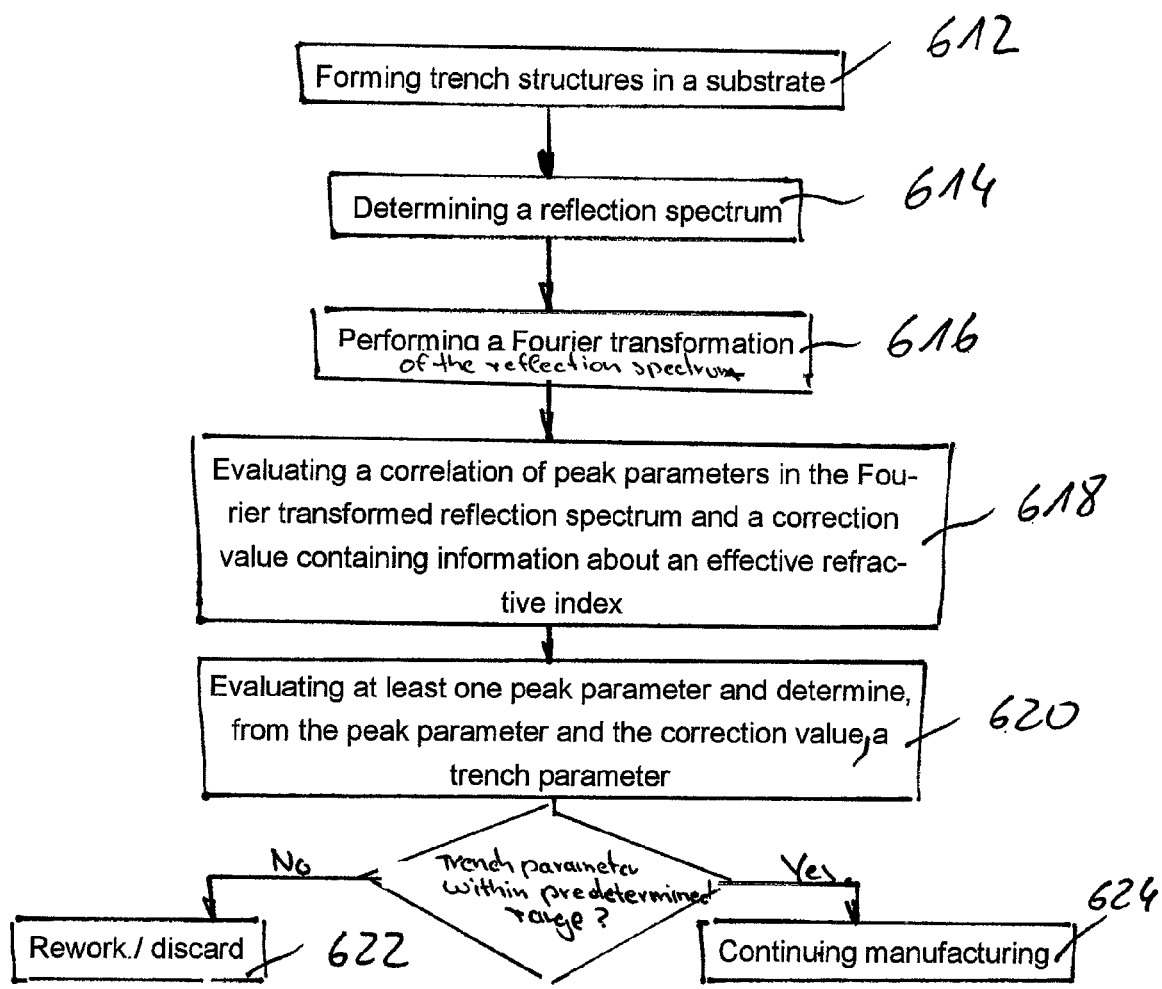
FIG. 11B is a simplified flow-chart of a method of an exemplary method of manufacturing an integrated circuit.

FIG. 11B is a first simplified flow-chart illustrating a method of manufacturing integrated circuits according to a further embodiment. Trench structures are formed in a substrate that is suitable for the manufacture of integrated circuits, for example a semiconductor wafer (612). A reflection spectrum, for example the reflectance spectrum or a phase change spectrum of infrared radiation that is reflected off the substrate is determined (614). The reflection spectrum is Fourier transformed to determine the Fourier transformed reflection spectrum (616). Further, a correlation of peak parameters of peaks in the Fourier transformed reflection spectrum and a correction value is evaluated, wherein the correction value contains information about an effective refractive index of a section of the substrate above a bottom edge of the trench structures (618). The correction value depends on the effective refractive index. The correction value may be, for example, the effective refractive index. At least one of the peak parameters is determined and from the peak parameter and the correction value, one of the trench parameters of the trench structures is evaluated (620). If the trench parameter is outside a predetermined range, for example falls below a lower limit or exceeds an upper limit, the substrate may be reworked or discarded (622). If the trench parameter does not fall below the lower limit and does not exceed the upper limit, such that the trench parameter is within the predetermined range, the process of manufacturing integrated circuits is continued (624).

Figure 12:
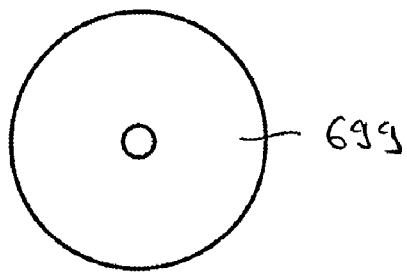
FIG. 12 shows an exemplary embodiment of a computer program product.

FIG. 12 is a simplified illustration of a computer program product 699 that comprises a computer storage and a program code mechanism that is embedded in the computer storage medium. The program code mechanism comprises a transformation code device configured to Fourier transform a reflection spectrum of infrared radiation reflected off a sample and a calculator code device that is configured to determine, from a parameter of a peak in the Fourier transformed reflection spectrum, a parameter of a trench structure in the sample.

According to an embodiment, the computer program product may further comprise a correlation data device that is configured to hold a correlation information which links effective refractive indices of a plurality of samples comprising trench structures on the one hand and peak parameters in Fourier transformed reflection spectra assigned to the plurality of samples on the other hand. The calculator code device may be configured to determine, at least inherently, an effective refractive index of the sample from the correlation information and the peak parameters of the Fourier transformed reflection spectrum.

While the invention has been described in detail and with reference to specific embodiments thereof, it will be apparent to one skilled in the art that various changes and modifications can be made therein without departing from the spirit and scope thereof. Accordingly, it is intended that the present invention covers the modifications and variations of this invention provided they come within the scope of the appended claims and their equivalents.

What is claimed:

1. An apparatus comprising:
   a peak detection unit configured to determine at least one peak parameter of a peak in a Fourier transformed reflection spectrum of infrared radiation reflected off a sample that comprises trench structures; and
   an evaluation unit configured to determine, from the at least one peak parameter and from an effective refractive index of the sample, a trench parameter of the trench structures; and
   a step analyzer unit configured to determine an orientation of different steps in trench structures via the phase of the reflection spectrum, wherein different steps in the trench structures define trench sidewall sections that extend toward or away from an axial center of the trench structures in relation to other trench sidewall sections.

2. The apparatus of claim 1, further comprising:
   a transformation unit configured to determine, from a reflection spectrum of the infrared radiation reflected off the sample, the Fourier transformed reflection spectrum.

3. The apparatus of claim 2, further comprising:
   an analyzer unit configured to determine the reflection spectrum of the reflected infrared radiation reflected off the sample.

4. The apparatus of claim 3, wherein the analyzer unit is configured to determine reflection spectrum as one of a reflectance spectrum, an amplitude spectrum, a power spectrum, a phase change spectrum, an amplitude change spectrum and a power change spectrum.

5. The apparatus of claim 1, further comprising:
   a storage unit that stores correlation information describing a correlation between effective refractive indices of a plurality of different samples comprising trench structures and peak parameters in Fourier transformed reflection spectra assigned to the plurality of different samples;
   wherein the evaluator unit is further configured to determine, from the correlation information, a correction value that contains information about the effective refractive index of the sample.

6. The apparatus of claim 1, wherein the peak detection unit is configured to assign a peak in the Fourier transformed reflection spectrum of infrared radiation reflected off the sample to a fragmented reflection plane corresponding to a bottom edge of the trench structures.

7. The apparatus of claim 5, wherein the evaluator unit is configured to evaluate the correction value using a model based fitting algorithm.

8. The apparatus of claim 1, wherein the evaluator unit is configured to determine the trench parameter as an average trench depth of the trench structures based upon the effective refraction index and an optical path difference between portions of the reflected infrared radiation.

9. An apparatus comprising:
   a peak detection unit configured to determine at least one peak parameter of a peak in a Fourier transformed reflection spectrum of infrared radiation reflected off a sample that comprises trench structures; and
   an evaluation unit configured to determine, from the at least one peak parameter and from an effective refractive index of the sample, a trench parameter of the trench structures as an average trench volume that is based upon a peak shift that results from different fill materials in the trench structures and from the refractive indices of the different fill materials.

10. An apparatus comprising:
    a peak detection unit configured to determine at least one peak parameter of a peak in a Fourier transformed reflection spectrum of infrared radiation reflected off a sample that comprises trench structures; and
    an evaluation unit configured to determine, from the at least one peak parameter and from an effective refractive index of the sample, a trench parameter of the trench structures as an average trench volume expansion coefficient that is based upon a peak shift resulting from a volume expansion in the trench structures.

11. A metrology apparatus comprising:
    an infrared radiation detection device configured to detect an infrared radiation reflected off a sample comprising trench structures;
    an analyzing device configured to determine a reflection spectrum of the reflected infrared radiation;
    a transformation device configured to determine, from the reflection spectrum, a Fourier transformed reflection spectrum;
    a calculator device configured to determine, from a parameter of a peak in the Fourier transformed reflection spectrum and from an effective refractive index of a section of the sample above a bottom edge of the trench structures, a trench parameter of the trench structures; and
    a step analyzing device configured to determine an orientation of a step in the trench structures via the phase of the reflection spectrum, wherein the step in the trench structures defines a trench sidewall section that extends toward or away from an axial center of the trench structures in relation to other trench sidewall sections.

12. The apparatus of claim 11, wherein the calculator device is configured to determine, from a position of the peak, an optical path difference between portions of the reflected infrared radiation.

13. The apparatus of claim 12, further comprising:
a storage device that stores correlation information that links information about effective refractive indices of a plurality of different samples comprising trench structures to peak parameters in Fourier transformed reflection spectra assigned to the plurality of samples;
wherein the calculator device is further configured to determine, from the peak parameters and the correlation information, a correction value that contains information about the effective refractive index of the sample.

14. The apparatus of claim 11, wherein the analyzing device is configured to determine the reflection spectrum as one of a reflectance spectrum, an amplitude spectrum, a power spectrum, a phase change spectrum, an amplitude change spectrum and a power change spectrum.

15. The apparatus of claim 11, wherein the transformation device and the calculator device are integrated into a single processor.

16. The apparatus of claim 11, wherein the infrared radiation detection device is configured to measure the intensity and/or polarization state of infrared radiation reflected from the sample.

17. The apparatus of claim 11, further comprising:
an infrared radiation emitting device configured to irradiate the sample with infrared radiation.

18. The apparatus of claim 11, further comprising:
a model-based fitting unit configured to compare and match trench parameter values determined from a model with trench parameter values that are determined by the calculator device.

19. The apparatus of claim 12, wherein the calculator device is configured to calculate the trench parameter as an average trench depth of the trench structures based upon the optical path difference and the correction value.

20. The apparatus of claim 11, wherein the calculator device is configured to calculate the trench parameter as an average trench volume of the trench structures based upon a peak shift resulting from different fill materials in the trench structures and from the refractive indices of the different fill materials.

21. A method of manufacturing integrated circuits, the method comprising:
forming trench structures in a substrate suitable for the manufacture of integrated circuits; and
performing a spectrometrologic method to determine the trench parameter of the trench structures, wherein the spectrometrologic method comprises:
determining a reflection spectrum of infrared radiation reflected off a substrate that includes trench structures;
performing a Fourier transformation of the reflection spectrum to determine a Fourier transformed reflection spectrum;
evaluating a correlation of peak parameters in the Fourier transformed reflection spectrum and a correction value containing information about an effective refractive index of a section of a sample above a bottom edge of the trench structures; and
evaluating at least one peak parameter of a peak in the Fourier transformed reflection spectrum to determine, from the peak parameter and the correction value, a trench parameter of the trench structures;
wherein the trench parameter is an average trench volume of the trench structures that is determined by:
determining a first position of the peak with a first material with a first refractive index filling the trench structure;
filling the trench structures with a second material with a second refractive index which is different from the first refractive index; and
determining, from a resulting peak shift and from the first and second specific refractive index, the average trench volume.

22. The method of claim 21, further comprising:
reworking or discarding the substrate when the trench parameter falls outside of a predetermined range.

23. The method of claim 21, wherein the trench parameter is an average trench depth of the trench structures that is determined based upon an optical path difference and the effective refractive index, wherein the optical path difference is determined from the position of the peak between portions of the reflected infrared radiation.

24. The method of claim 21, wherein the evaluating of the correlation of peak parameters in the Fourier transformed reflection spectrum comprises:
determining a peak value of at least one calibration sample comprising trench structures; and
measuring an average trench depth of the trench structures of the at least one calibration sample via optical analysis methods.

25. The method of claim 21, wherein the reflection spectrum is one of a reflectance spectrum, an amplitude spectrum, a power spectrum, a phase change spectrum, an amplitude change spectrum and a power change spectrum.

26. The method of claim 21, further comprising:
defining a starting model for a model-based fitting algorithm using the determined trench parameter.

27. A method of manufacturing integrated circuits, the method comprising:
forming trench structures in a substrate suitable for the manufacture of integrated circuits; and
performing a spectrometrologic method to determine the trench parameter of the trench structures, wherein the spectrometrologic method comprises:
determining a reflection spectrum of infrared radiation reflected off a substrate that includes trench structures;
performing a Fourier transformation of the reflection spectrum to determine a Fourier transformed reflection spectrum;
evaluating a correlation of peak parameters in the Fourier transformed reflection spectrum and a correction value containing information about an effective refractive index of a section of a sample above a bottom edge of the trench structures; and
evaluating at least one peak parameter of a peak in the Fourier transformed reflection spectrum to determine, from the peak parameter and the correction value, a trench parameter of the trench structures;
wherein the trench parameter is an average trench volume difference and wherein the method further comprises:
determining a first position of the peak;
expanding the trench structures;
determining a second position of the peak;
determining, from the first and second position, a peak shift of the peak in the Fourier transformed spectrum;
determining, from the peak shift, a new effective refractive index of the substrate portion; and
calculating the average trench volume difference of the trench structures before and after expanding the trench structures from the new effective refractive index and the specific refractive indices of materials embedding the trench structures and materials filling the trench structures.

28. A computer program product, comprising:
a non-signal computer storage medium; and
a program code mechanism embedded in the non-signal computer storage medium and comprising a calculator code device configured to determine, from a parameter of a peak in a Fourier transformed reflection spectrum and an effective refractive index of a section of a sample comprising trench structures, a trench parameter of the trench structures as an average trench volume that is based upon a peak shift that results from different fill materials in the trench structures and from the refractive indices of the different fill materials.

29. The computer program product of claim 28, further comprising:
a transformation code device configured to Fourier-transform a reflection spectrum of the reflected infrared radiation.

30. The computer program product of claim 28, further comprising:
a correlation data device configured to store correlation information linking information about effective refractive indices of a plurality of samples comprising trench structures to peak parameters in Fourier transformed reflection spectra assigned to the plurality samples;
wherein the calculator code device is configured to determine, from the correlation information and from peak parameters of the Fourier transformed reflection spectrum, a correction value that contains information about the effective refractive index of the sample.

31. The computer program product of claim 30, wherein the correlation information is embedded in the non-signal computer storage medium.

* * * * *